United States Patent [19]

Shigeta et al.

[11] Patent Number: 4,722,893
[45] Date of Patent: Feb. 2, 1988

[54] REAGENTS FOR ENZYME IMMUNOASSAY FOR APOLIPOPROTEIN B

[75] Inventors: Yukio Shigeta, Kusatsu; Yutaka Harano, Otsu; Takamitsu Nakano, Kusatsu; Hideo Nishikawa, Minoo, all of Japan

[73] Assignee: Shiraimatsu Shinyaku Kabushiki Kaisha, Shiga, Japan

[21] Appl. No.: 627,714

[22] Filed: Jul. 5, 1984

[30] Foreign Application Priority Data

Jul. 6, 1983 [JP] Japan ................... 58-123973

[51] Int. Cl.⁴ ............... G01N 33/535; G01N 33/546; G01N 33/547; G01N 33/563
[52] U.S. Cl. ........................... 435/7; 435/188; 435/810; 436/512; 436/533; 436/534; 436/815
[58] Field of Search ............ 435/7, 28, 188, 810; 436/512, 533, 594, 815

[56] References Cited

U.S. PATENT DOCUMENTS

| | | | |
|---|---|---|---|
| 4,342,739 | 8/1982 | Kakimi et al. | 436/823 |
| 4,399,217 | 8/1983 | Holmquist et al. | 435/188 |
| 4,433,059 | 2/1984 | Chang et al. | 436/520 |
| 4,467,031 | 8/1984 | Gallati et al. | 436/813 |

OTHER PUBLICATIONS

Yoshitake et al., Chemical Abstracts, 98:3339b (1983), 305.
Imagawa et al., Chemical Abstracts, 97:142813u (1982), 504.
Fievet et al., Clin. Chem., 30(1): 98–100 (Jan. 1984).
Yolken, Reviews of Infections Diseases, 4(1): 35–68, Jan.–Feb. 1982.
Jean Charles Fruchart et al., "Enzyme Immunoassay for Human Apolipoprotein B, the Major Protein Moiety in Low-Density-and Very-Low-Density Lipoproteins" *Clinical Chemistry*, vol. 24, No. 3, 1978 pp. 455–459.

*Primary Examiner*—Esther M. Kepplinger
*Attorney, Agent, or Firm*—Armstrong, Nikaido, Marmelstein & Kubovcik

[57] ABSTRACT

Reagents for enzyme immunoassay for apolipoprotein B comprising human apolipoprotein B as a standard antigen, peroxidase-labeled Fab' as an antibody, IgG-coated polystyrene balls, a coloring or fluorescent reagent, hydrogen peroxide as a reaction substrate, a reaction stopper, and buffer solutions.

Use of these reagents permits accurate and prompt quantification of apolipoprotein B concentration in serum.

8 Claims, 2 Drawing Figures

REAGENTS FOR ENZYME IMMUNOASSAY FOR APOLIPOPROTEIN B

BACKGROUND OF THE INVENTION

The present invention relates to reagents for quantification of apolipoprotein B concentration in serum by enzyme immunoassay using sandwich method.

Hyperlipidemia plays a significant role in the causation of atherosclerosis. More specifically, an increase in the low-density lipoprotein (LDL) fractions or a decrease in the proportion of high-density lipoproteins (HDL) is considered to be an important indicator leading to atherosclerosis. While HDL-cholesterol measurement is generally used for clinical examination purposes, measurement of LDL-cholesterol or apolipoprotein B concentration is not in general use for such examination, because LDL measurement requires a prolonged ultra-centrifugation process.

In view of the fact that apolipoprotein B, as the major apoprotein component of LDL, represents as much as about 98% of the total apoprotein contents of LDL, the present inventors contemplated measuring apolipoprotein B concentration accurately and on a mass measurement basis to provide a marker as to the atherogenesity of LDL concentration.

In addition to that included in LDL, apolipoprotein B is partially contained in very-low-density lipoproteins (VLDL), but the apolipoprotein B content of VLDL is about 1/20 of that of LDL. Therefore, apolipoprotein B largely reflects LDL. In recent years, it has been recognized that VLDL and more particularly $\beta$-VLDL are also contributory to atherosclerosis. As such, measurement of apolipoprotein B contained in both LDL and VLDL is therefore clinitically useful.

A highly sensitive measurement technique is also essential for detection of diseases involving decrease in LDL or VLDL concentration in plasma, such as lipoprotein B deficiency, liver diseases and intestinal deseases with absorption disorders.

At some facilities, techniques such as radial immunodiffusion (SRID) and rocket immunoelectrophoresis are employed in measuring apolipoprotein B concentration in serum. However, these methods have their disadvantages. The former method is rather low in sensitivity (30-200 mg/dl), and it requires visual evaluation which involves considerable variation according to the person who makes the determination. Therefore, it is unsuitable for multispecimen evaluation. The later method requires troublesome electrophoresis and it is rather complicated.

Another method known as radioimmunoassay (RIA) technique may be considered, but this method has not yet been developed well to practical application. Moreover, the fact that the method uses a radioactive isotope ($^{125}$I) involves various problems, such as radiation exposure and accumulation possibilities, a certain qualification required in practicing the method, expensive facility and equipment required, short half life of the isotope which means short service life thereof, possible environmental pollution, and limitations on waste disposal. Therefore, it is impractical to use the RIA technique for a regular clinical examination purposes.

As a measurement technique which involves no use of such radioactive material there is available a method known as enzyme immunoassay. However, no method of the type has yet been reported which can meet such practical requirements as high accuracy, good sensitivity, ease of control, and simplicity.

We have therefore developed an enzyme immunoassay which dissolves the above problems.

The present invention has as its object the provision of practically advantageous reagents for evaluation of apolipoprotein B concentration in human serum by enzyme immunoassay.

SUMMARY OF THE INVENTION

The reagents for enzyme immunoassay for apolipoprotein B in accordance with the present invention comprise:

| | |
|---|---|
| human apolipoprotein B as a standard antigen | (1); |
| peroxidase-labeled Fab' as an antibody | (2); |
| IgG-coated polystyrene balls | (3); |
| a coloring or fluorescent reagent | (4); |
| hydrogen peroxide as a reaction substrate | (5); |
| a reaction stopper | (6); and |
| buffer solutions | (7). |

It has now been found that the above-mentioned defects of conventional methods can be completely eliminated and the object of the present invention can be attained by providing said reagents.

DESCRIPTION OF THE INVENTION

Figure 1:
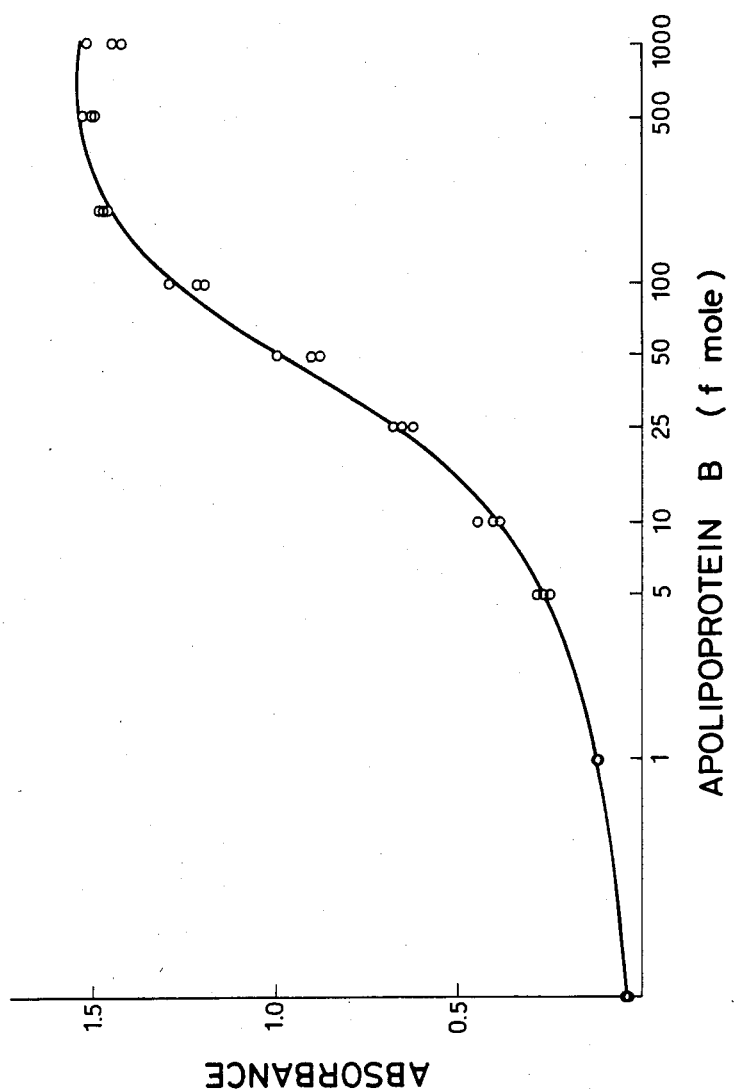
FIG. 1 is a graphical representation showing the relation between absorbance and apolipoprotein B concentration.

As above stated, the reagents for enzyme immunoassay for apolipoprotein B in accordance with the invention comprise:

| | |
|---|---|
| human apolipoprotein B as a standard antigen | (1); |
| peroxidase-labeled Fab' as an antibody | (2); |
| IgG-coated polystyrene balls | (3); |
| a coloring or fluorescent reagent | (4); |
| hydrogen peroxide as a reaction substrate | (5); |
| a reaction stopper | (6); and |
| buffer solutions | (7). |

Provision of these reagents as a kit permits determination of apolipoprotein B under the following procedures and mechanism. That is, the IgG-coated polystyrene ball is introduced into a mixture of standard solution or dilute specimen solution and buffer solution so that apolipoprotein B contained in the standard solution or diluted specimen solution is coated to IgG on the polystyrene ball by antigen-antibody reaction. Then, the ball is dipped into the buffer solution in which peroxidase-labeled Fab' has been dissolved, and by antigen-antibody reaction the Fab' side of the peroxidase-labeled Fab' is allowed to bind with the apolipoprotein b which has already joined with the ball. That is, the peroxidase-labeled Fab' is bound to the apolipoprotein B which is in bond with the IgG on the polystyrene ball. After this reaction process, the polystyrene ball is placed into the coloring or fluorescent reagent solution, followed by addition of hydrogen peroxide as an enzyme reaction substrate. Then, the peroxidase acts on the coloring or fluorescent reagent to produce a coloring or fluorescent material. After some suitable period of time, the reaction stopper is added and the concentration of the product is determined by absorbance or fluorescence measurement. Comparison of the measurements with a calibration curve previously determined with reference materials can readily tell accurate level of the apolipoprotein B concentration.

Components of the reagent kit according to the present invention and their roles will now be described in detail.

One of the reagents constituting the kit of the invention is human apolipoprotein B (1). The apolipoprotein B is prepared by refining LDL (low-density lipoprotein) fractionated by centrifugation from human serum, further refinement being carried out by such method as dialysis or column chromatography. Generally, LDL contains about 98% of apolipoprotein B, and refinement of LDL can provide an essentially pure apolipoprotein B. The apolipoprotein B thus obtained is used as a standard antigen. As will be described hereinafter, it is also used for preparation of antibody IgG and fragment Fab'.

Another component of the reagent kit is peroxidase-labeled Fab' (2). This reagent is prepared in the following manner.

Refined LDL as obtained as aforesaid, that is apolipoprotein B, is intradermally injected, together with an adjuvant (Freund's complete adjuvant in particular), into an animal having relatively large antibody forming power (New Zealand white rabbit in particular), and further, apolipoprotein B is intravenously injected several times within a suitable period of time. After a suitable period, blood samples are collected to obtain antiserum.

The antiserum is passed through separation and refinement steps, including salting out, centrifugation, dialysis, and column chromatography, to obtain immunoglobulin, IgG, an antibody. As is well known, IgG consists of two polypeptide chains, each having a molecular weight of about 23000 (light chains) and two polypeptide chains, each having a molecular weight of about 50000 (heavy chains).

Pepsin, a proteolytic enzyme, is caused to act on the IgG, whereby the IgG is subjected to fractionation through column chromatography or the like. Fragment F(ab')$_2$ is thus obtained. Then, the F(ab')$_2$ is reacted for reduction in a phosphate buffer solution containing a stabilizer (ethylenediaminetetraacetate in particular) and a reducing agent (mercaptoalkylamine in particular). Subsequently, the product is subjected to column chromatographic fractionation. A fragment Fab' having antigen bonding activity is thus obtained. That is, by reducing S—S bond at a hinge of F(ab')$_2$ into Fab', preparation is made to facilitate enzyme attachment. The reducing agent used in this reaction process changes bond —SS— to —SH HS—, and the stabilizer serves to stabilize Fab' which has been changed in structure to —SH.

Perhaps most suitable for use in labeling the Fab' with peroxidase is the maleimide method. According to this method, N-hydroxysuccinimide ester of N-(4-carboxycyclohexylmethyl)maleimide is used to introduce a maleimide group into peroxidase, and a thiol radical of the Fab' is reacted with the group. Another method available is the periodate method, which is such that an aldehyde group produced by oxidizing peroxidase with periodate is reacted with the amino group of Fab', the resulting Schiff base being reduced. A method called glutaric aldehyde method may also be used.

According to the present invention, peroxidase is used as a labeling enzyme. Other types of enzymes than peroxidase were also examined for use, but peroxidase was found most preferable.

A further component of the reagent kit is IgG-coated polystyrene ball (3). The IgG-coated polystyrene ball has antibody IgG supported on a polystyrene ball so that its reaction with apolipoprotein B, an antigen in the specimen, can be effected in solid phase. An IgG-coated polystyrene ball may be prepared in such a way that IgG as obtained in aforesaid manner is dissolved in a buffer solution, then a polystyrene ball having a suitable diameter is placed in the solution and left to stand, and subsequently removed therefrom.

In the present invention, it is essential that a polystyrene ball is used as a support member for bond with IgG. Use of other supports such as polystyrene tube inner wall, silicone rubber piece, disc or rod, and aminoalkyl silyl glass rod was also examined as to advisability thereof, but polystyrene ball was found most preferable.

Another component reagent of the kit is a coloring or fluorescent reagent (4). This reagent develops color or fluorescence under the action of the labeling peroxidase. Available for use as coloring reagents are 3,3',5,5'-tetramethylbenzidine, o-phenylenediamine, 5-aminosalicylate, o-phenyldiamine dihydrochloride, 2,2'-azino-di-(3-ethylbenzthiazoline)-6'-sulfonic acid, and o-dianisidine. Among these, 3,3',5,5'-tetramethylbenzidine is particularly preferable which exhibits good accuracy. Among items available as fluorescent reagents are thyramine and p-hydroxyphenyl propionate.

These coloring or fluorescent reagents are changed into luminescent or fluorescent materials by the action of peroxidase. Hydrogen peroxide is needed as one of the substrates for this enzyme reaction. That is, the following reaction is utilized.

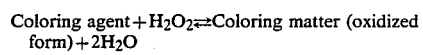

Coloring agent + $H_2O_2$ ⇌ Coloring matter (oxidized form) + $2H_2O$

A reaction stopper is needed for stopping enzyme reaction at a suitable time. So, the reagent kit of the invention also includes hydrogen peroxide (5) as a reaction substrate, and a reaction stopper (6). Suitable for use as reaction stopper are acids such as sulfuric acid and hydrochloric acid, and alkalis. Hydrogen peroxide (5) may be premixed with the coloring or fluorescent reagent (4).

Use of a buffer solution is essential in carrying out the above described steps. Therefore, the reagent kit includes buffer solutions (7). Available for the purpose is a phosphate buffer solution mixed with sodium chloride, bovine serum albumin, and sodium azide as required.

The present invention is more particularly described and explained by means of the following Examples.

EXAMPLE 1

Apolipoprotein B

Human serum was centrifuged by employing an ultra-centrifugal separator (Hitachi, Ltd., 70P-72, vertical rotor, (RPV50T)) at 50,000 rpm for 2.5 hr, LDL being sampled. After subjected to dialysis with a 5 mM phosphate buffer (pH 4), the LDL was concentrated in a collodion bag, and the concentrate was subjected to fractionation by using Biorad's A-5m (1 cm diameter, 120 cm high), refined LDL being thus obtained. The refined LDL was essentially pure apolipoprotein B, and examination by SDS (sodium dodecylsulfate)-polyacrylamide gel electrophoresis indicated an apolipoprotein B band in a region of molecular weight of 500,000.

IgG

Forty milligram of the refined LDL thus obtained, that is apolipoprotein B, was dissolved in 5 ml buffer solution. The resulting solution was mixed with 5 ml of Freund's complete adjuvant. A total of 10 mg/2.0 ml of the mixture was intradermally injected into a New Zealand white rabbit, at a total of 10 to 20 locations thereof, and 2 weeks later, 2 mg/0.2 ml of a solution prepared by dissolving the apolipoprotein B to a buffer solution was intravenously injected into the rabbit (first intravenous injection). Subsequently, at two-week intervals, similar intravenous injections were carried out two times. (A total of three intravenous injections, 2 mg each of apolipoprotein B, were made per rabbit.) On the 10th day of the third intravenous injection, 20 ml of blood was collected to obtain antiserum.

0.18 g of sodium sulfate per 1 ml of the antiserum was added bit by bit for salting out, and then centrifugal separation was carried out at 10,000 rpm for 10 min to obtain a precipitate. The precipitate was dissolved with 1 ml of 0.0175M phosphate buffer (pH 6.3). The resulting solution was dialyzed against same buffer. After dialysis, fractionation was carried out by employing a diethylaminocellulose column and IgG was obtained.

F(ab')$_2$

The IgG thus obtained was dialyzed against a 0.1M sodium acetate buffer (pH 4.5) (10-20 mg IgG/1 ml of buffer). Then, 0.05 ml solution of 2M sodium chloride was added to the dialyzed IgG solution, and again, pepsin was added at a ratio of 0.4 mg/10 mg of IgG. After reaction was carried out at 37° C. for 20 hr, the pH was adjusted to 8, and by employing Pharmacia Sephadex G-150 column, elution was carried out in a 0.1M sodium borate buffer (pH 8.0), F(ab')$_2$ being thus obtained.

Fab'

0.3 mg of F(ab')$_2$ was dissolved in 0.45 ml of a 0.1M phosphate buffer (pH 6.0). To the above solution was added a 0.1M phosphate buffer (mixed with 5 mM sodium ethylenediaminetetraacetate and 0.1M 2-mercaptoethylamine) (pH 6.0) in a quantity corresponding to 1/9 of that of the former (0.05 ml), and reaction was carried out at 37° C. for 1.5 hr. Then, the resulting solution was applied to a Sephadex G-25 column (1 cm diameter, 30 cm high) and elution was carried out in a 0.1M phosphate buffer (pH 6.0), Fab' being thus obtained.

Maleimide Peroxidase 6 mg of peroxidase was dissolved in 1 ml of 0.1M phosphate buffer, and then 2.5 mg/100 μl dimethylformaldehyde solution of 50 times molar volume (relative to peroxidase) N-hydroxysuccinimide ester of N-(4-carboxycyclohexylmethyl)maleimide was added. Reaction was carried out at 30° C. for 30 min. The reaction mixture was eluted in a 0.1M phosphate buffer (pH 6.0) by employing a Sephadex G-25 column (1 cm diameter, 45 cm high), maleimide peroxidase being thus obtained.

Peroxidase-Labeled Fab'

50 μM of Fab' and 50 μM of maleimide peroxidase were mixed in equal quantities. After incubation at 30° C. for 1 hr, the mixture was eluted in a 0.1M phosphate buffer (pH 6.5) by employing a Ultrogel AcA-44 (LKB, 1.5 cm diameter, 45 cm high), peroxidase-labeled Fab' being thus obtained. Evaluation of individual fractions was made by measuring protein quantities at 280 nm and peroxidase quantities at 403 nm using spectrophotometer, and by measuring peroxidase activity.

IgG-Coated Polystyrene Ball

The IgG as obtained in aforesaid manner was adjusted so that it makes a 100 μg/ml buffer solution. Polystyrene balls of 6.5 mm diameter were placed in the solution at a rate of 80-100 pieces/20 ml, and were allowed to stand overnight at 4° C. so that IgG was coated on the ball surfaces.

Coloring Reagent

A 134 μg/ml aqueous solution of 3,3',5,5'-tetramethylbenzidine was prepared as coloring reagent.

Reaction Substrate, Reaction Stopper, Buffer Solution

A 0.01% aqueous solution of hydrogen peroxide was prepared as a reaction substrate.

An aqueous solution of 2M sulfuric acid was prepared as a reaction stopper.

A buffer solution of the following composition:
0.01M phosphate buffer of pH 7.0;
0.1M NaCl; and
0.1% bovine serum albumin was prepared (hereinafter "buffer A"). For the purpose of diluting standard antigen and/or serum specimen, 0.1% sodium nitrite may sometimes be added to buffer A.

Operating procedures are as follows:

1. 200 μl of standard solution or dilute specimen solution and 100 μl of buffer A are poured into a test tube and one of the IgG-coated polystyrene ball is introduced into the tube and allowed to stand overnight at 4° C.

2. The solution is removed by suction and then the ball is washed twice with 2 ml of buffer A. Into a test tube containing 200 ng/300 μl of peroxidase-labeled Fab', the washed ball is added and then incubated at 20° C. for 3 hr.

3. After removal of the solution by suction, the ball is washed twice with 2 ml of buffer A, then, the ball is placed in a test tube containing 600 μl of 3,3',5,5'-tetramethylbenzidine solution (concentration 134 μg/ml) and subjected to preincubation at 30° C. for 5 min.

4. Next, 200 μl of 0.01% aqueous solution of hydrogen peroxide is added into the tube and reaction is carried out at 30° C. for 10 min. Then, 40 μl of the aqueous solution of 1M sulfuric acid is added to stop reaction.

5. Absorbance at 450 nm is determined. Concentration of the specimen is determined according to the standard curves. Fluorescence intensity is determined at 320 nm for excitation and at 404 nm for emission.

A solution of human apolipoprotein B as standard antigen (standard solution) and serum samples (specimen) prepared in such a way that 2 ml each of blood collected from patients visiting Shiga University of Medical Science Hospital is centrifuged and preserved at 4° C. are assayed all at one time in manner as above described.

The relationship between absorbance and various concentrations of standard apolipoprotein B is shown in FIG. 1. In the figure, ordinates axis represent absorbance and abscissae axis represent apolipoprotein B concentration, the curve being a calibration curve. It is noted that f mole means $10^{-15}$ mol/100 μl.

Apolopoprotein B concentrations of the specimens were determined by using the calibration curve. The results are shown in Table below.

| Disease | No. of cases | Apolipoprotein B concentration (mg/dl) |
|---|---|---|
| Normal subjects | 20 | 83.4 ± 20.3 |
| Diabetes (type II)* | 59 | 125 ± 33.8 |
| Type IIa hyperlipidemia | 3 | 203 ± 59.5 |
| Type IV hyperlipidemia | 2 | 132 ± 40.3 |
| Liver cirrhosis | 1 | 26 |
| Acromegaly | 1 | 112 |

*Of the patients suffering from diabetes (type II) 60-70% had signs of atherosclerosis.

EXAMPLE 2

Measurements were made in the same manner as in Example 1, except that fluorescent reagent was used instead of coloring reagent. That is, a styrene ball was preincubated in 250 μl of 0.1% solution of p-hydroxyphenyl propionate, then 50 μl of an aqueous solution of 0.03% hydrogen dioxide was added, and the reaction was carried out at 30° C. for 30 min. Subsequently, 0.1M glycin-NaOH solution (pH 10) was added to stop the reaction.

Figure 2:
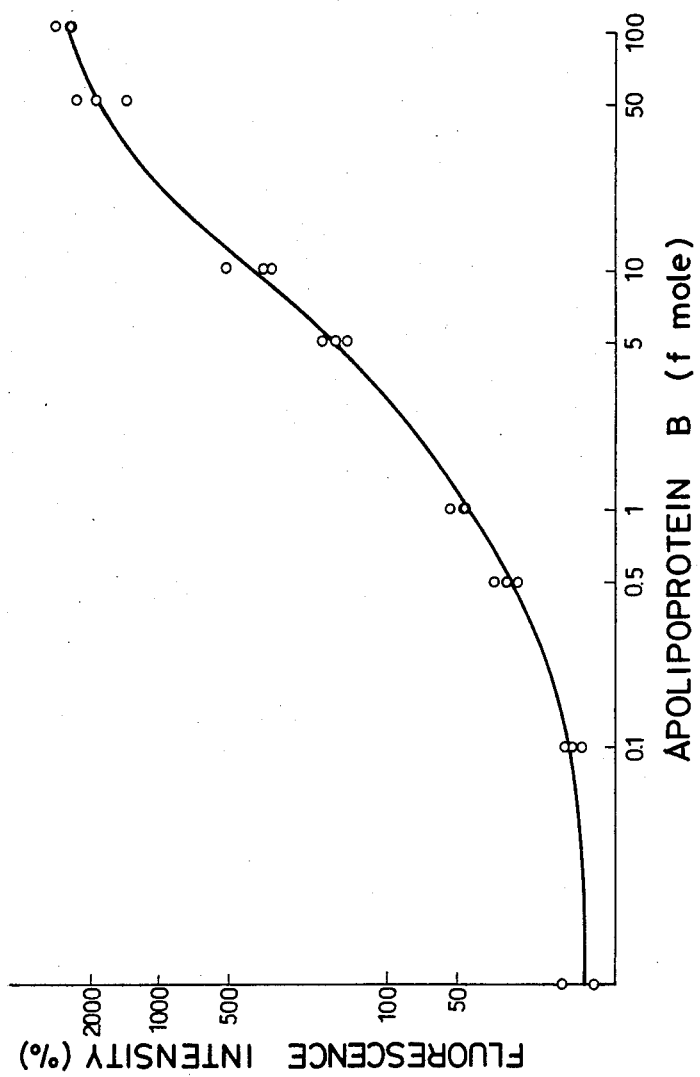
FIG. 2 is a graph showing the relation between fluorescence intensity and apolipoprotein B concentration.

The relationship between fluorescence intensity and various concentrations of standard apolipoprotein B is shown in FIG. 2. In the figure, ordinates axis represent fluorescence intensity and abscissae axis represent apolipoprotein B concentration, the curve being a calibration curve.

What is claimed is:

1. Reagents for enzyme immunoassay for apolipoprotein B comprising the following components to be used together to perform the immunoassay:
   human apolipoprotein B as as standard antigen,
   peroxidase-labeled Fab' specific to apolipoprotein B as an antibody,
   polystyrene balls coated with IgG which will join with apolipoprotein B by a antigen-antibody reaction,
   a coloring or fluorescent reagent selected from the group consisting of 3,3',5,5'-tetramethylbenzidine, o-phenylenediamine, 5-aminosalicylate, o-phenyldiamine dihydrochloride, 2,2'-azinodi-(3-ethylbenzthiazoline)-6'-sulfonic acid, thyramine and p-hydroxyphenyl propionate,
   hydrogen peroxide as a reaction substrate,
   a reaction stopper, and
   buffer solutions.

2. Reagents as claimed in claim 1, wherein said peroxidase-labeled Fab' consists of peroxidase bound to the Fab' by a maleimide method wherein said peroxidase labeled Fab' is a product produced by the introduction of a maleimide group into peroxidase and a thiol radical of said Fab' is reacted with said group.

3. A method for the enzyme immunoassay of apolipoprotein B comprising:
   (a) coating polystyrene particles with serum immunoglobulin G (IgG) raised against apolipoprotein B;
   (b) immersing one or more of said coated polystyrene particles in a serum or saline solution containing apolipoprotein B and a buffer solution containing Fab' specific to apolipoprotein B which Fab' is chemically bound to an peroxidase;
   (c) transferring said polystyrene particles to a solution containing hydrogen peroxide and, optionally, a reagent selected from the group consisting of 3,3',5,5'-tetramethylbenzidine, o-phenylenediamine, 5-aminosalicylate, o-phenyldiamine dihydrochloride, 2,2'-azinodi-(3-ethylbenzthiazoline)-6' sulfonic acid thyramine and p-hydroxyphenyl propionate;
   (d) chemically stopping the enzymatic reaction; and
   (e) measuring the absorption of light or the fluorescence of a enzymatically changed substrate or of the product of the reaction between the enzymatically changed substrate and the reagent.

4. The method of claim 3 in which the enzymatic reaction with the substrate is stopped with an acid or an alkali.

5. A kit for the determination of apolipoprotein B in serum comprising a package containing the following components to be used together for determining apolipoprotein B:
   (a) an apolipoprotein B standard;
   (b) polystyrene balls coated with IgG raised against apolipoprotein B;
   (c) peroxidase-labeled Fab' specific to apolipoprotein B; and
   (d) hydrogen peroxide and a reagent which reacts with an enzymatically changed substrate to give a product having a color or a product which fluoresces wherein said reagent is selected from the group consisting of 3,3',5,5'-tetramethylbenzidine, o-phenylenediamine, 5-aminosalicylate, o-phenyldiamine dihydrochloride, 2,2'-azinodi-(3-ethylbenzthiazoline)-6'-sulfoninc acid, thyramine and p-hydroxyphenyl propionate.

6. A kit according to claim 5 which also includes a stopper solution and reconstitutable buffer.

7. A kit according to claim 5 in which the polystyrene balls are spheres having a diameter between about 2 and about 10 mm.

8. A method for the determination of apolipoprotein B in a serum sample, comprising:
   (a) preparing a saline buffer containing bovine serum albumin;
   (b) mixing the apolipoprotein B standard, one or more IgG-coated polystyrene balls and peroxidase-labeled Fab' with buffer;
   (c) incubating the mixture;
   (d) separating the polystyrene balls from the solution and washing the polystyrene balls in buffer;
   (e) incubating the polystyrene balls in a solution containing hydrogen peroxide and a reagent which is selected from the group consisting of 3,3',5,5'-tetramethylbenzidine, o-phenylenediamine, 5-aminosalicylate, o-phenyldiamine dihydrochloride, 2,2'-azinodi-(3-ethylbenzthiazoline)-6'-sulfonic acid, o-dianisidine, thyramine and p-hydroxyphenyl propionate;
   (f) stopping the reaction;
   (g) measuring the absorbance of light or the fluorescence of the stopped solution;
   (h) repeating steps (b) through (g) with a different concentration of apolipoprotein B;
   (i) performing steps (b) through (g) with a sample containing blood serum, and
   (j) calculating the amount of apolipoprotein B in the serum sample.

* * * * *